US00PP29107P2

(12) United States Plant Patent
Smith

(10) Patent No.: US PP29,107 P2
(45) Date of Patent: Mar. 13, 2018

(54) *CHRYSANTHEMUM* PLANT NAMED 'CIFZ0037'

(50) Latin Name: *Chrysanthemum×morifolium*
Varietal Denomination: CIFZ0037

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 87 days.

(21) Appl. No.: 14/998,571

(22) Filed: Jan. 20, 2016

Related U.S. Application Data

(60) Provisional application No. 62/161,924, filed on May 15, 2015.

(51) Int. Cl.
*A01H 5/02* (2006.01)

(52) U.S. Cl.
USPC ..... Plt./288

(58) Field of Classification Search
USPC ..... Plt./288, 287, 289
CPC ..... A01H 5/0255; A01H 5/02; A01H 5/00
See application file for complete search history.

(56) References Cited

U.S. PATENT DOCUMENTS

PP14,725 P2 * 4/2004 Hofmann ..... Plt./288
PP21,205 P3 * 8/2010 Blom ..... Plt./288

* cited by examiner

*Primary Examiner* — June Hwu
(74) *Attorney, Agent, or Firm* — Dale Skalla

(57) ABSTRACT

A new garden type *Chrysanthemum* plant named 'CIFZ0037' particularly distinguished by the medium to large sized white, decorative-type flowers, vigorous growth habit with a rounded, mounding plant habit, and with the natural flowering season in early September.

1 Drawing Sheet

Latin name of the genus and species of the plant claimed: *Chrysanthemum×morifolium.*

Varietal denomination: 'CIFZ0037'.

BACKGROUND OF THE NEW PLANT

The present invention comprises a new *Chrysanthemum*, botanically known as *Chrysanthemum×morifolium*, and hereinafter referred to by the variety name 'CIFZ0037'.

'CIFZ0037' is a product of a planned breeding program. The new cultivar has medium to large, white, decorative-type inflorescences, a natural flowering season in early September, and vigorous growth habit with a rounded, mounding plant habit.

'CIFZ0037' originated from a hybridization made in February 2007 in Tenjo, Columbia. The female parent was the commercial variety 'Yojacqueline' (U.S. Plant Pat. No. 18,927), with light lavender flower color, smaller inflorescences with fewer disc florets, a natural season response that is slower by one week, and with a similar or somewhat smaller plant size and a more perfectly round plant habit when compared to 'CIFZ0037'.

The male parent of 'CIFZ0037' was the commercial variety 'Dreamstar Hami', not patented in the United States, with smaller, yellow flowers with more disc florets, a similar flowering response, rounder plant habit and smaller overall size when compared to 'CIFZ0037'.

The resultant seed was sown in June 2007 in Alva, Fla., USA, and 'CIFZ0037' was selected as a single flowering plant within the progeny of the stated cross on Oct. 26, 2007.

The first act of asexual reproduction of 'CIFZ0037' was accomplished when vegetative stem cuttings were propagated from the initial selection in December 2007 in Alva, Fla.

BRIEF SUMMARY OF INVENTION

Horticultural examination of plants grown from cuttings of the plant initiated in Alva Fla. in June 2008, in a trial applying black cloth, and continuing thereafter, has demonstrated that the combination of characteristics as herein disclosed for 'CIFZ0037' are firmly fixed and are retained through successive generations of asexual reproduction.

'CIFZ0037' has not been observed under all possible environmental conditions. The phenotype may vary significantly with variations in environment such as temperature, light intensity and day length.

'CIFZ0037' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0037' with colors being as true as possible with an illustration of this type.

DETAILED BOTANICAL DESCRIPTION

Figure 1:
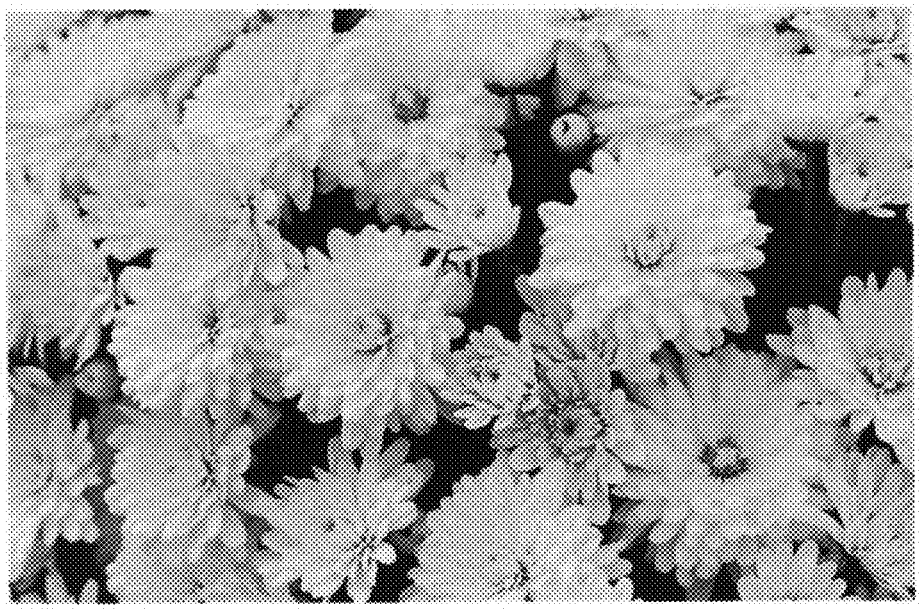

The aforementioned photographs: FIG. 1 is a close-up of the inflorescence in buds, when opening and fully opened taken on Sep. 9, 2014, in Monroeville, N.J., one rooted cutting planted Jun. 25, 2014 in a 9 inch pot, not pinched, and allowed to naturally come into flower.

Figure 2:
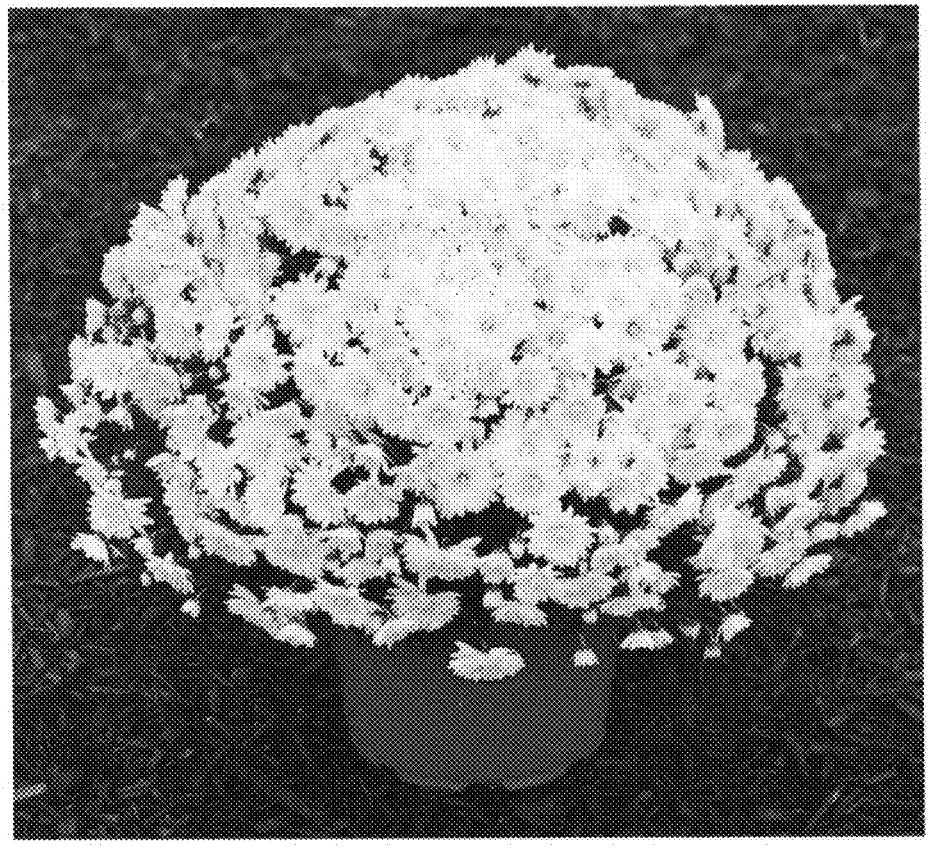

FIG. 2 is a pot culture of the claimed plant showing its growth habit from a similar trial in 2013 and was taken on Sep. 18, 2013. One rooted cutting was planted Jun. 19, 2013 in a 9 inch pot, not pinched, and allowed to naturally come into flower.

Color references are made to The Royal Horticultural Society Colour Chart (R.H.S.) 2001.

TABLE 1

DIFFERENCES BETWEEN THE NEW VARIETY 'CIFZ0037' AND TWO MOST SIMILAR VARIETIES:

| | 'CIFZ0037' | 'YOTIFFANY' (U.S. Plant Pat. No. 17,425) |
|---|---|---|
| Flowering response (natural season and use of blackcloth): | Similar | Similar |
| Flower color: | Similar | Similar |
| Inflorescence, shape: | Decorative-type with more disc florets | Decorative-type no disc florets |
| Inflorescence, size: | Similar or slightly smaller | Similar or slightly larger |
| Plant habit or size: | Similar habit but larger and stronger plant | Smaller plant height |

| | 'CIFZ0037' | 'ZANMUSPEN' (U.S. Plant Pat. No. 21,205), commercially 'Aspen White' |
|---|---|---|
| Inflorescence: | Similar color and size, with more disc florets | Similar color and size, no disc florets |
| Natural flowering response: | 1 week faster | 1 week slower |
| Plant habit and size: | Similar habit, but larger when grown under the same environmental conditions | Smaller when grown under the same environmental conditions |

The plant descriptions and measurements were taken on an indoor trial in Enkhuizen, The Netherlands in October 2015 on about 13 weeks old plants. Rooted cuttings had been planted, 1 plant per pot, in 19 cm pots in week 31, 2015. The plants were not pinched. Short daylight started week 39 until week 41.

Plant:

*Form, growth and habit.*—Herbaceous garden-type, stems upright and outwardly spreading, freely branching, strong and moderately vigorous growth habit.

*Plant height* (*above soil*).—18 cm.

*Plant height* (*inflorescence included*).—25 cm.

*Plant width.*—35-40 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 137C.

*Immature leaf, color lower surface.*—RHS 137D.

*Mature leaf, color, upper surface.*—RHS 137A.

*Mature leaf, color lower surface.*—RHS 137B.

*Length.*—4.6 cm.

*Width.*—4.5 cm.

*Shape.*—Ovate, with distinct lobes.

*Base shape.*—Attenuate.

*Apex shape.*—Acute.

*Margin.*—3 lobed (palmate), edge serrate.

*Texture, upper surface.*—Puberulous.

*Texture, lower surface.*—Hirsute, more dense at veins.

*Color of veins, upper surface.*—RHS 147B.

*Color of veins, lower surface.*—RHS 147B.

*Pattern of veining.*—Palmate.

*Petiole color.*—RHS 144B.

*Petiole Length.*—1.1-1.2 cm.

*Diameter.*—0.15-0.4 cm.

*Texture.*—Densely covered with hairs, tomentose.

*Leaf stipule.*—No leaf stipule.

*Lobe depth.*—Average.

Stem:

*Quantity of main branches per plant.*—3 to 6.

*Color of stem.*—RHS 147B.

*Length of stem.*—15-20 cm.

*Diameter.*—0.5 cm.

*Length of internodes.*—2-4 cm.

*Texture.*—Tomentose.

*Color of peduncle.*—RHS 147B.

*Length of peduncle.*—3-7 cm.

*Peduncle diameter.*—0.2 cm.

*Texture.*—Densely covered with hairs.

Inflorescence:

*Type.*—Compositae, solitary, decorative-type inflorescences borne terminally above foliage, ray florets arranged acropetally on a capitulum giving a daisy eyed double flower form.

*Quantity of short days to flowering* (*response time*).—Approximately six weeks.

*Natural season flowering.*—Early September.

*Quantity of inflorescences per plant.*—300-400 (roughly).

*Lastingness of individual blooms on the plant.*—About five weeks from first color.

*Fragrance.*—Slightly spicy.

*Number of ray floret whorls.*—Approximately 7.

*Pistil.*—Ray and Disc Florets.

Bud (when showing color):

*Color.*—1D with tips bit darker 3C.

*Length.*—1 cm.

*Width.*—1 cm.

*Shape.*—Oblate (almost globular).

Immature inflorescence:

*Diameter.*—3 cm.

*Color of ray florets, upper surface.*—RHS 155A for outer florets, RHS 5C-D for the center.

*Color of ray florets, lower surface.*—Close to RHS 4D.

Mature inflorescence:

*Diameter.*—4.5-5 cm.

*Depth.*—1.5 cm.

*Total diameter of disc.*—0.3-0.5 cm.

*Receptacle color.*—RHS 147B.

*Receptacle height.*—0.4 cm.

*Receptacle diameter.*—1.5 cm.

Ray florets:

*Average quantity of florets.*—Between 200-400 in several whorls.

*Color of florets, upper surface* (*adaxial*).—Outer whorls RHS 155B white, inner whorls closer to disc RHS 4D.
*Color lower surface* (*abaxial*).—Whiter than RHS 155A.
*Length.*—2.2 cm.
*Width/diameter.*—0.6 cm; 0.1 cm for the tube at the Base.
*Ray floret tube*.—Short.
*Shape*.—All spatulate when mature.
*Apex shape*.—Mostly obtuse.
*Base shape*.—Tube.
*Margin*.—Entire, small incisions may occur at the tip.
*Texture, upper surface*.—Papillate.
*Lower surface*.—Papillate.

Disc florets:
*Average quantity of florets*.—Between 100 and 200, only appearing when flower is fully opened.
*Color.*—14B.
*Length.*—0.8 cm.
*Width.*—0.2 cm.
*Shape*.—Tubular, elongated.
*Apex shape*.—Acute, 5 pointed.

Phyllaries:
*Quantity.*—20-30.
*Color, upper surface*.—RHS 147B.
*Color, lower surface*.—RHS 147B.
*Length.*—0.7 cm.
*Width.*—0.2-0.3 cm.
*Shape*.—Lanceolate.
*Apex shape*.—Acute.
*Base*.—Fused.
*Margins*.—Entire.
*Texture, upper surface*.—Glabrous.
*Texture, lower surface*.—Densely covered.

Reproductive organs:
*Pistil*.—One.
*Length.*—0.4 cm.
*Style color*.—RHS 155D.
*Style length.*—0.3 cm.
*Stigma color*.—RHS 13B.
*Stigma shape*.—Bi-parted.
*Ovary color*.—RHS 4D.
*Ovary length.*—0.15 cm.
*Ovary width.*—0.1 cm.

Androecium:
*Stamens.*—1, found on only disc florets.
*Color of filaments*.—RHS 1D.
*Length filaments.*—0.15 cm.
*Anther color*.—RHS 14B.
*Anther length.*—0.15-0.2 cm.
*Anther shape*.—Oval to club shaped.
*Color of pollen*.—RHS 14B.
*Pollen amount*.—Moderate.
*Fertility/seed set*.—Has not been determined to date.
*Disease/pest resistance*.—Has not been determined to date.
*Plant hardiness zone and heat cold resistance*.—Not measured.

What is claimed is:

1. A new and distinct variety of *Chrysanthemum* plant named 'CIFZ0037' substantially as illustrated and described herein.

* * * * *